United States Patent [19]

Weissman

[11] 4,306,866

[45] Dec. 22, 1981

[54] ADJUSTABLE DENTAL DRILL GUIDE

[75] Inventor: Bernard Weissman, New York, N.Y.

[73] Assignee: IPCO Corporation, White Plains, N.Y.

[21] Appl. No.: 136,534

[22] Filed: Apr. 2, 1980

Related U.S. Application Data

[63] Continuation-in-part of Ser. No. 70,247, Aug. 27, 1979.

[51] Int. Cl.³ .............................................. A61C 5/00
[52] U.S. Cl. ...................................................... 433/215
[58] Field of Search ...................... 433/72, 76; 408/46, 408/72, 241, 115, 72 B

[56] References Cited

U.S. PATENT DOCUMENTS

| 1,136,100 | 4/1915 | Chayes | 433/72 |
| 3,276,326 | 10/1966 | Gibbons et al. | 408/72 |
| 3,292,494 | 12/1966 | Anderson et al. | 408/72 |
| 3,417,471 | 12/1968 | Mitchell | 433/72 |

*Primary Examiner*—Robert Peshock
*Attorney, Agent, or Firm*—Friedman, Goodman & Teitelbaum

[57] ABSTRACT

An adjustable dental drill guide for locating and permitting the drilling of accurately spaced apart holes for receiving a dental retaining splint. The drill guide includes two telescopically arranged portions which can be secured together in a preselected extended position to form a composite rigid body member. A locating pin depends from the distal end of one of the portions for being received in a hole provided in a first tooth when the body member is disposed in a channel extending from the first tooth to at least one adjacent tooth. A drill bushing passes through the distal end of the other body portion and extends upwardly therefrom for guiding a drill during formation of a hole in an adjacent tooth. Preferably, the body portion provided with the locating pin is a bar, and the body portion provided with the drill bushing is a hollow member for slidably receiving the bar therein. In a modified form, the locating pin has a shoulder portion thereon for permitting the drill guide to pivot when associated with a track member.

7 Claims, 15 Drawing Figures

ADJUSTABLE DENTAL DRILL GUIDE

RELATIONSHIP TO OTHER APPLICATIONS

This application is a continuation-in-part application of Ser. No. 070,247 filed Aug. 27, 1979 for a "Dental Retaining Splint", the entire disclosure of which is herein incorporated by reference.

BACKGROUND OF THE INVENTION

This invention relates to dentistry in general, and more particularly to an adjustable dental drill guide for locating holes to be drilled in dentition so as to receive a dental retaining splint for the reinforcement of the dentition.

The use of dental splints generally requires a high degree of skill, and in the prior art such splints have been limited in their use. Because of the requirement for involved and complicated procedures in the preparation of the teeth, as well as the limitations involved in the splint structure itself, the use of such splints has in the past been restricted. In many cases they were used only with anterior teeth where horizontal parallelism of the splint could be achieved. Additionally, the time involved and the discomfort to the patient has also prevented widespread use of such splinting devices.

An improved dental retaining splint which avoids many of the prior art problems was described in the aforementioned co-pending parent application. Such dental retaining splint has an elongated bar-like member with a number of tubular members extending therefrom. The splint is first temporarily held in a channel formed in adjacent teeth with the tubular members extending upwardly from the teeth. The tubular members have axial openings therethrough and such axial openings are used as guides for a drill to form pilot holes in the teeth. The splint is then removed and the pilot holes function as lead holes for the formation of enlarged bores to receive the tubular members therein. The splint is then repositioned in the channel so that the tubular members are now disposed downwardly into the bores formed therefor. An inlay fills the channel and covers the splint in the final procedure step.

While such a retaining splint has expanded the possibility of utilizing splinting devices for the reinforcement of dentition, in many situations the length of a required splint will not be in accordance with a predetermined standard size. In certain situations the teeth may be so large that the size of the splint which is required is longer than the standard size. Additionally, when a splint is required to extend across more than two teeth, the splint will have to be made with at least one arcuate section so as to conform to the arcuate arrangement of the teeth. This will require bending and shaping of the dental splint to conform to the desired arc. Also, in utilizing the dental splint of the aforementioned co-pending parent application, it is necessary to securely retain the splint in the channel during the formation of the pilot holes. Typically, dental wax is used for such retention. However, by utilizing such dental wax, additional discomfort, time, and manipulating is required of the patient's teeth which may frequently be undesirable.

Additionally, even when utilizing dental splints of the type described in the aforementioned parent application, it is frequently desired to modify the spacing between the bores in order to avoid drilling into the pulp tissue of the teeth. By utilizing predetermined lengths of the dental splints, it is not always feasible to provide such facility for adjustment of the spacing between the bores.

SUMMARY OF THE INVENTION

Accordingly, it is an object of the present invention to provide in dental drill guide which can be utilized to adjust, to a desired distance, the spacing between bores to be drilled in the teeth.

Another object of the present invention is to provide an adjustable dental drill guide which can be used in the formation of holes for receiving a dental retaining splint.

A further object of the present invention is to provide an adjustable dental drill guide which can be used in the formation of bores so as to receive a dental retaining splint of the type described in the parent application.

Still another object of the present invention is to provide an adjustable dental drill guide which can be utilized to locate and drill holes of a desired spacing therebetween.

Yet another object of the present invention is to provide an adjustable dental drill guide which can be used in the formation of holes in order to properly position a dental splint across more than two adjacent teeth.

A further object of the present invention is to provide a dental drill guide which permits the formation of a hole in a tooth adjacent to other teeth already having a dental retaining splint.

Still a further object of the present invention is to provide an adjustable dental drill guide which provides for simple adjustment of the length of the guide so as to permit proper adjustment of the spacing between holes to be formed in teeth.

Yet another object of the present invention is to provide an adjustable dental drill guide having telescoping sections with a locating pin on one section and a drill bushing or tube on the other section.

These objects are achieved in accordance with a preferred embodiment of the present invention wherein the adjustable dental drill guide comprises an elongated hollow member with an elongated bar telescopically received in the hollow member. A locking device is provided for securing the bar within the hollow member at a preselected extended position in order to form a composite rigid body member. A locating pin depends from the distal end of the bar for being received in a hole provided in a first tooth while the body member is disposed in a channel extending from the first tooth to at least one adjacent tooth. A drill bushing or tube passes through the distal end of the hollow member and extends upwardly therefrom for guiding a drill during the formation of a hole in an adjacent tooth.

The invention further contemplates the addition of a shoulder at the base of the locating pin, and at the same time extending the drill bushing downwardly from the hollow member. In this way, the body member can be spaced above the channel bottom. This will facilitate the use of the drill guide when extending an existing dental splint to the next adjacent tooth whereby the drill guide can be positioned into the existing dental splint.

In the dental procedure, the channel is formed across at least two adjacent teeth and a hole is drilled in a first one of the teeth. The hole can already exist as part of a previously installed dental splint. The extended position of the telescopic body portions of the dental drill guide are then adjusted to obtain the desired spacing to the next hole to be drilled. The drill guide is then disposed on the teeth with the body portions positioned in the channel and the locating pin positioned in the previously drilled hole. A new hole is then drilled in the adjacent tooth by using the drill bushing extending from the body portion as a drill guide. The temporary disposition is achieved without the use of retaining wax. The dental drill guide is then removed from the teeth and a new splint or splint extension can then be utilized, as the specific case may require. An inlay then fills in the channel to cover the splint.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings of a preferred embodiment in which.

In the various figures of the drawings, like reference characters designate like parts.

DETAILED DESCRIPTION OF THE PREFERRED EMBODIMENTS

Figure 1:
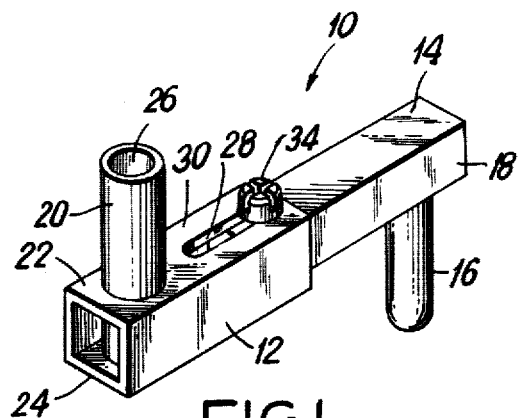
FIG. 1 is a perspective view illustrating an adjustable dental drill guide in accordance with a first embodiment of the present invention.
Figure 2:
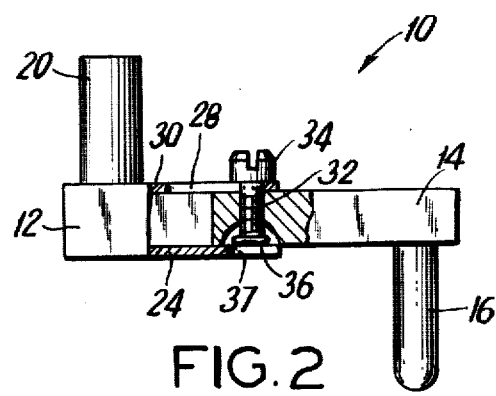
FIG. 2 is a side view, partially broken away, of the drill guide shown in FIG. 1.
Figure 3:
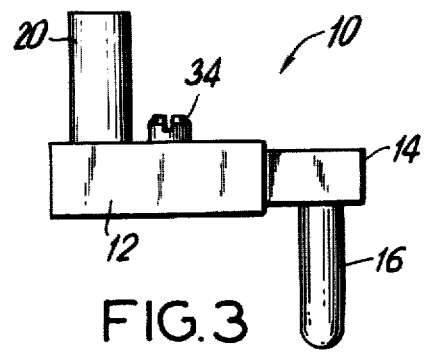
FIG. 3 is a side elevational view of the dental drill guide in an adjusted position.

Referring now to the drawings, FIGS. 1, 2 and 3 show an adjustable dental drill guide 10, according to the present invention. The drill guide comprises a square hollow member 12, and a square bar 14 which is telescopically received within the hollow member, where the square configurations prevent rotation therebetween. A cylindrical locating pin 16 depends perpendicularly from the distal end 18 of the bar 14. A drill bushing or tube 20 upwardly extends perpendicularly from the distal end 22 of the hollow member 12, passing through the end so as to terminate at the bottom wall 24 of the hollow member 12. Accordingly, the locating pin 16 and drill bushing 20 are in a parallel arrangement. An axial opening 26 extends entirely through the drill bushing.

An elongated slot 28 is formed in the upper wall 30 of the hollow member. A screw 32 is threaded into a threaded hole provided in the bar 14, the screw passing through the elongated slot 28. The enlarged head 34 of the screw is disposed against the upper wall 30 of the hollow member. The opposite end of the screw is flattened to provide a flange 36 to capture the screw between the hollow member and the bar. The flange 36 sits under the bar 14, typically in a countersunk hole. It is noted that the bottom wall 24 of the hollow member is provided with a slot 37 so that the flange 36 can be formed after the screw is threaded into the bar.

The bar 14 can be slidably positioned within the hollow member 12 so as to provide a desired extension therefrom, as indicated by different extensions shown in FIGS. 2 and 3. The screw 32 is then turned so that the enlarged head 34 is tightened against the upper wall 30 to rigidly secure the bar within the hollow member and thereby provide a substantially rigid body member.

Figure 4:
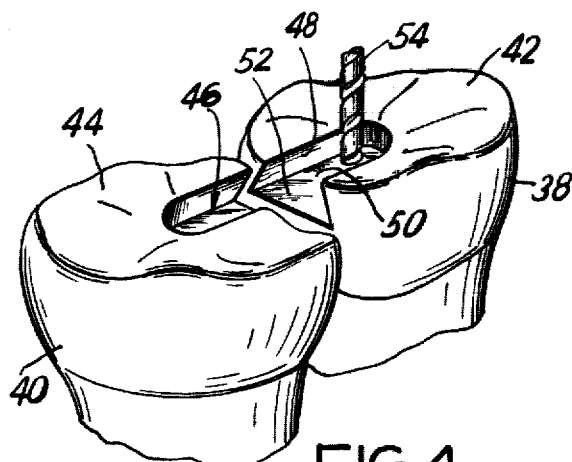
FIG. 4 is a perspective view illustrating two adjacent teeth provided with a channel and showing the first step in utilizing the drill guide of the present invention.
Figure 5:
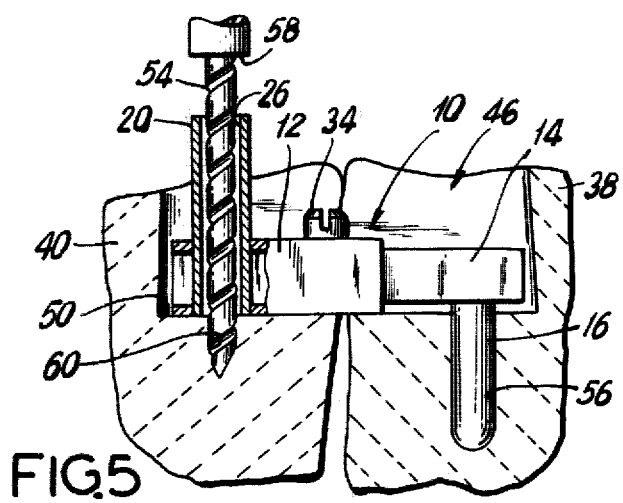
FIG. 5 is an elevational view, partly in cross section, illustrating the positioning of the dental drill guide in the channel and the formation of a hole in the teeth using the drill bushing as a guide.

Referring now to FIGS. 4 and 5, the operation of the adjustable drill guide will be described. FIG. 4 shows adjacent teeth 38, 40, such as for example the adjacent bicuspids. It is understood that the present invention is equally applicable to and between other adjacent teeth, such as the cuspids, the molars, etc. In each occlusal surface 42, 44 a connecting channel 46 is formed therebetween in a conventional manner. Preferably, the walls 48 of the channel are tapered to provide a wide bottom wall 50 at the base 52 of the channel, where the tapered walls act to retain the inlay of dental material within the channel, as will be set forth hereinafter below. It is understood that the channel 46 is oversized to be larger than the splint to be utilized both in its length, width and height.

After the channel is formed, a drill bit 54 is utilized to drill a first hole 56 in one of the teeth. The hole can be drilled by approximating the suitable position by means of the eye. It is not necessary to use a drill guide or bushing for the initial hole. However, if desired any of the well known drill bushings can be utilized to suitably position even the first hole.

After the first hole 56 is drilled, the adjustable dental drill guide 10 is adjusted for a proper extended length so that a suitable spacing will be obtained between the holes. The screw is then turned so that the head 34 is tightened against the hollow member 12 to rigidly secure the bar 14 to the hollow member 12. The rigid body is then placed in the channel 46 so that the bottom of the hollow member 12 is disposed against the bottom wall 50 of the channel, and the locating pin 16 is inserted in the hole 56, which was first drilled.

The drill bushing 20 is then utilized as a guide for the formation of a hole 60 in the adjacent tooth 40, as shown in FIG. 5. The drill bit 54 generally has a predetermined length in order to obtain the desired depth for the hole 60. Accordingly, the drill 54 can be provided with a stop wall abutment 58 which will contact the upper portion of the drill bushing 20 when the desired depth for the hole 60 has been reached. It is noted that the diameter of the drill 54 is substantially equal to or slightly larger than the diameter of the locating pin 16 so that the hole 56 can receive the locating pin.

After the hole 60 has been made, the adjustable dental drill guide is removed. It should be noted that no retaining wax was necessary in order to hold the adjustable drill guide in place. It was simply inserted on the bottom of the channel and, by means of the retaining pin 16, was held in place for the drilling operation.

Once the holes 56, 60 have been drilled, a retaining splint can then be inserted across the adjacent teeth. Such a retaining splint 62 is shown generally in FIG. 6, and includes a substantially rectangular bar-like body member 64 having downwardly depending retaining pins 66, 68 perpendicularly extending from the bottom wall 70 thereof. A retaining splint of the type shown in FIG. 6 can easily be pre-molded using standard techniques for molding a splint in accordance with well known dental principles.

Figure 7:
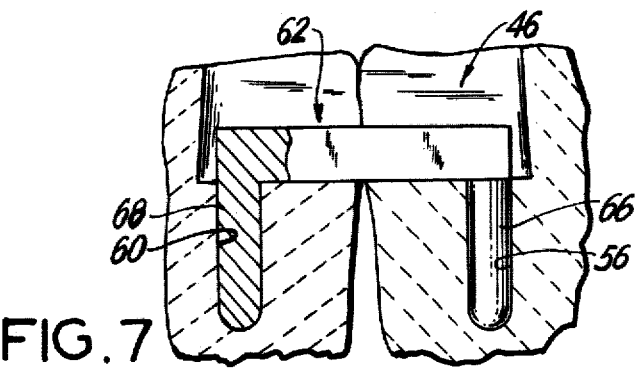
FIG. 7 is an elevational view, partly in cross section, illustrating the positioning of the dental retaining splint in the channel so as to function as a reinforcing member.

The splint 62 can then be inserted into the channel 46 with the pins 66, 68 respectively being positioned in the drilled holes 56, 60, as shown in FIG. 7, where the pins 66, 68 are sized to be received in the holes 56, 60. Inlay material can then be disposed in the channel 46 over the dental splint 62 to cover and complete the dental procedure. Such dental inlays are well known in the dentistry art.

Figure 6:
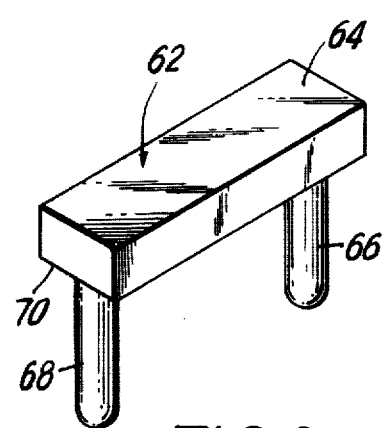
FIG. 6 is a perspective view of a dental retaining splint which can be utilized in conjunction with the present invention.

Instead of utilizing a pre-molded dental splint of the type shown in FIG. 6, it is possible to utilize the dental retaining splint of the type described in the aforementioned co-pending parent application. Accordingly, the holes 56, 60 which were drilled, can be utilized to enlarge the holes in order to form suitable sized bores. The bores can then receive the tubular members of the body portion of the dental retaining splint described in the aforementioned parent application.

For convenience, as indicated above, in order to utilize the same drill bit 54, and in order for the retaining pins 66, 68 of the splint to be of the same size, the outside diameter of the locating pin 16 should be approximately equal to the internal diameter of the axial opening 26 formed in the drill bushing 20. In this way, the holes 56, and 60 will be substantially identical.

The embodiments heretofore described can be utilized when initially providing a dental retaining splint between adjacent teeth. Frequently, it is necessary to provide such a dental splint between three or more adjacent teeth where there is provided an arcuate curvature in the channel extending across the teeth. The drill guide 10 can also be utilized in these situations. However, in many situations, a dental splint has already been inserted between at least two of these adjacent teeth and it is necessary to extend the splint to nearby additional adjacent teeth. In such cases, the dental retaining splint may already be in place and it is necessary to accurately space a new hole from the holes already existing which accommodate the existing dental splint. Accordingly, the drill guide 10 could be utilized with the splint for a straight inline new hole, but may not lend itself to the forming of an accurately spaced new hole as indicated below.

Figure 8:
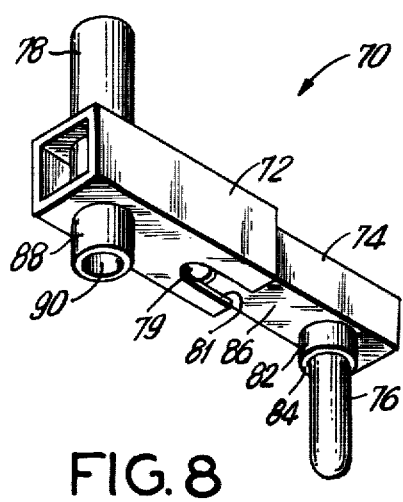
FIG. 8 is a perspective view illustrating another embodiment of the adjustable dental drill guide in accordance with the present invention.
Figure 9:
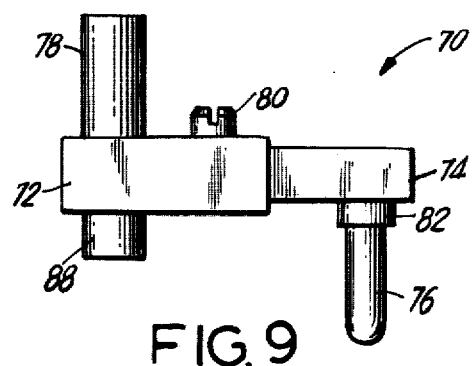
FIG. 9 is an elevational view of the adjustable drill guide shown in FIG. 8.

In order to facilitate utilization of the adjustable dental drill guide in the formation of an accurately spaced new hole where a splint is already in place, a modification can be made as is shown in FIGS. 8 and 9. In these figures there is described an adjustable dental drill guide 70 again including a square hollow member 72 which telescopically receives therein a square bar 74. A locating pin 76 depends perpendicularly from the lower surface of the bar and the drill bushing or tube 78 extends perpendicularly through the distal end of the hollow member 72, so that the locating pin 76 and drill bushing 78 are in a parallel arrangement. A suitable locking mechanism, such as the captive screw, having a flattened flange 79 at one end, can again be utilized to rigidly secure the bar within the hollow member. The enlarged head 80 of the screw is used to tighten the parts together. Again, a slot 81 is provided in the hollow member so that the screw end can be flattened.

In the embodiment shown, a circular collar 82 is located about the base portion of the locating pin 76. The collar has an abutting surface 84 at its outer end and its inner end is positioned directly against the base surface 86 of the bar 74.

The drill bushing or tube 78 extends upwardly from the hollow member 72, passing therethrough as in the previous embodiment. However, it now extends beneath the hollow member so as to form an extension 88 downwardly depending therefrom. The axial opening 90 extends entirely through the drill bushing 78.

Figure 10:
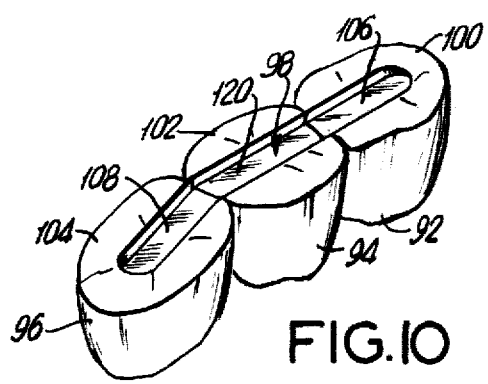
FIG. 10 is a perspective view illustrating three adjacent teeth provided with a channel in which a dental retaining splint is to be inserted.

Referring now to FIGS. 10–13, the operation of the adjustable dental drill guide 70 of FIGS. 8 and 9 will be described. FIG. 10 shows three adjacent teeth 92, 94, 96. Again bicuspids are shown by way of example, the channel 98 being formed across the occlusal surfaces 100, 102, 104 of the three teeth. It will be noted, that the channel includes a substantially elongated section 106 extending across the teeth 92 and 94. The section 108 of the channel is angularly oriented with respect to the section 106. Such angular orientation can result from the arcuate arrangement of the teeth within the mouth structure. Alternately, it may result from a displacement of one of the teeth from its proper location.

Figure 11:
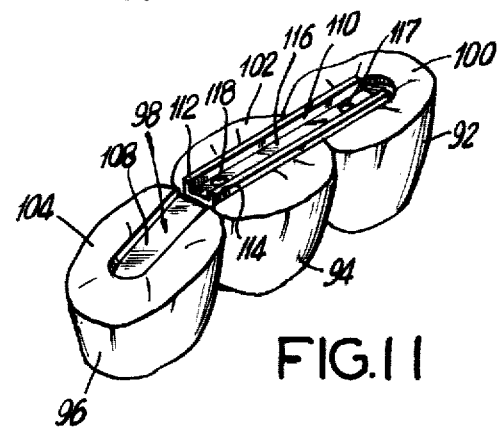
FIG. 11 is a perspective view of the teeth shown in FIG. 10, already including a dental retaining splint in two adjacent teeth.

As shown in FIG. 11, there has already been provided a dental splinting device 110 in the section 106 between the teeth 92, 94. Such splinting device can be of the type described in the aforementioned parent application. It will be noted that the splint 110 is substantially H-shape in a cross sectional configuration. The upper surface accordingly includes the sidewalls 112, 114 and the base wall 116. The tubular members (not shown in FIG. 11) are downwardly extending into the pre-formed holes in the teeth 92, 94 so as to retain the splint in place. The axial openings 117, 118 are shown extending through the tubular members.

The dental splint may have previously been formed as a result of previous work done on the teeth to retain the teeth 92 and 94 in secure relationship. It may now be desired to extend such a splint to the next adjacent tooth 96 so as to provide retention of the three teeth together. Alternately, it may be that the teeth are only being temporarily held together by means of the retaining splint. In such case, the retaining splint 116 may have only been utilized in order to form the holes in the adjacent teeth 92, 94, in accordance with the operation described in the aforementioned parent application.

In either case, it is now desired to provide a suitably located hole in the tooth 96. However, the difficulty is that the new hole must be suitably spaced from the existing opening 118 and the distance therebetween is along an arcuate path, or that the new hole is not in alignment with the openings 117, 118.

Figure 12:
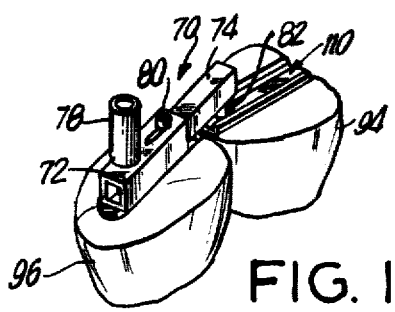
FIG. 12 is a perspective view of two adjacent teeth showing the positioning of the adjustable dental drill guide for use in extending the dental splint of FIG. 11 to the next adjacent tooth.

In order to accurately provide such spacing, the adjustable dental drill guide 70 is utilized. First, the spacing is properly arranged by selecting the proper extension of the bar 74 from the hollow member 72 and then locking the position by means of tightly engaging the head 80 of the screw against the hollow member. The locating pin 76 is then inserted directly into the opening 118 in the tubular member 119 of the splinting device 110. The collar 82 serves as a spacer to maintain the bar 74 positioned above the splinting device 110 so that the drill guide 70 can be pivoted, as shown in FIG. 12. The abutment wall 84 of the collar will be directed against the base wall 116 of the splinting device 110 and will be retained in place. The splinting device serves as a track for receiving the drill guide 70.

Figure 13:
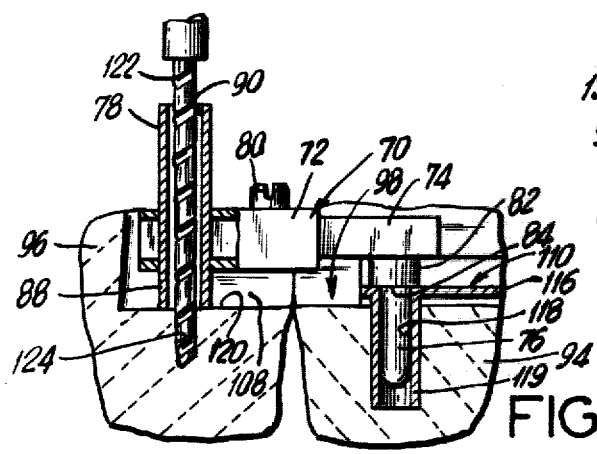
FIG. 13 is an elevational view, partly in cross section, illustrating the positioning of the adjustable dental drill guide in the teeth and showing the formation of a hole in the next adjacent tooth.

The tubing 72 will be spaced above the base 120 of the channel 98 by means of the extended end 88 of the drill bushing 78. Accordingly, the dental drill guide 70 will be positioned in a plane substantially parallel with the base 120 of the channel. The height of the downward extension 88 of the drill bushing 78 is almost approximately equal to the height of the walls of the retaining splint 110, being shorter by the thickness of the bottom wall of the hollow member, where the height of the collar 82 is much shorter, as shown in FIG. 9. With the adjustable dental drill guide 70 in position, the drill bit 122 can be inserted into the axial opening 90 of the drill bushing 78 to form the hole 124 in the tooth 96, as shown in FIG. 13.

Figure 14:
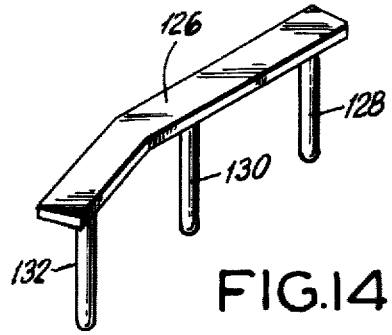
FIG. 14 is a perspective view of a dental retaining splint which can be utilized in the channel shown in FIG. 10.
Figure 15:
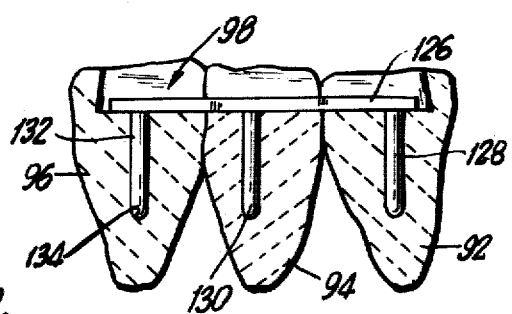
FIG. 15 is an elevational view illustrating the positioning of the retaining splint of FIG. 14 in the channel formed, so as to permanently function as a reinforcing member in the teeth.

After the holes are formed, the adjustable dental drill guide 70 is removed and a suitable splint can be inserted. The splint shown in FIG. 14 is a pre-molded splint having a body portion 126 with depending positioning pins 128, 130, 132. The specific shape is molded so as to correspond to the shape of the channel 98 and accordingly the arcuate shape of the teeth in which it is to be inserted. The splint shown in FIG. 14 can then be inserted into the teeth, as shown in FIG. 15. The pins 128 and 130 will be located in the holes that were previously formed for receiving the tubular members of the splint 110. The pin 132 will be located in a new hole 134 which is an enlargement of the pilot hole 124, whereby each of the pins have the same diameter so that the holes also must have the same diameter. Inlay material can then be placed to permanently mount the splint in place.

It is noted, that if the splint 110 is not used, there would be no reason to enlarge the pilot holes formed by the drill bit 122. Accordingly, the diameters of the pins 128, 130, 132 would be molded approximately the same size as the diameter of the drill bit 122 and the axial opening 90, the same as mentioned above with respect to the splint 62.

Although a particular molded splint was shown in FIGS. 14 and 15, it should be understood that the dental splinting device of the aforementioned parent application could be utilized. In fact, in such parent application there was described indentations formed on the sides of the splint body to specifically permit bending of the splint in order to conform to particular arcuate shapes of the type described in connection with the present embodiment.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. An adjustable dental drill guide comprising first and second elongated portions telescopically engaged together, locking means for securing said first and second elongated portions at any one of preselected extended positions to provide a composite rigid body member, a locating pin extending outwardly in a first direction from a distal end of said first elongated portion for being received in a hole provided in a first tooth when said body member is disposed in a channel extending from the first tooth to at least one adjacent tooth, a drill bushing passing through a distal end of said second elongated portion and extending outwardly therefrom in a second direction opposite said first direction for guiding a drill during formation of a hole in an adjacent tooth, and shoulder means disposed around a base of said locating pin for being received within a track member disposed in a portion of the channel to space said first elongated portion above the track member for permitting said body member to pivot relative to the track member.

2. An adjustable dental drill guide as in claim 1, wherein said first and second elongated portions have non-circular cross sectional configurations to prevent rotation therebetween.

3. An adjustable dental drill guide as in claim 1, wherein an outer diameter of said locating pin proximates an inner diameter of said drill bushing.

4. An adjustable dental drill guide as in claim 1, wherein said drill bushing is extended outwardly in said first direction to correspond to the height of the track member, whereby said body member can be retained in a plane substantially parallel with the bottom of the channel even with the presence of a track member in a part of the channel.

5. An adjustable dental drill guide as in claim 1, wherein said second elongated portion is a hollow member and said first elongated portion is a bar having a configuration which can slide within said hollow member.

6. An adjustable dental drill guide as in claim 5, and further comprising an elongated slot provided in a wall of said hollow member, and wherein said locking means includes a screw threaded in said bar and extending through said slot with an enlarged head of said screw being engageable against an outside surface of said wall of said hollow member.

7. An adjustable dental drill guide as in claim 5, wherein said locating pin is perpendicular to said bar and said drill bushing is perpendicular to said hollow member, said locating pin and said drill bushing being parallel to each other.

* * * * *